United States Patent [19]

Fjare et al.

[11] Patent Number: 5,166,424
[45] Date of Patent: Nov. 24, 1992

[54] LIQUID PHASE OXIDATION OF ALCOHOLS TO PREPARE CARBOXYLIC ACIDS

[75] Inventors: Kristi A. Fjare, Naperville; Calvin T. Chew, Warrenville, both of Ill.

[73] Assignee: Amoco Corporation, Chicago, Ill.

[21] Appl. No.: 810,713

[22] Filed: Dec. 18, 1991

Related U.S. Application Data

[63] Continuation-in-part of Ser. No. 672,970, Mar. 21, 1991, abandoned, which is a continuation-in-part of Ser. No. 279,429, Dec. 2, 1988, abandoned.

[51] Int. Cl.$^5$ .............................................. C07C 51/16
[52] U.S. Cl. .................................................... 562/538
[58] Field of Search ......................................... 562/538

[56] References Cited

U.S. PATENT DOCUMENTS 2,444,924  7/1948  Farkas .................................. 562/538
2,920,087  1/1960  Hay ..................................... 562/538

Primary Examiner—Arthur C. Prescott
Attorney, Agent, or Firm—Gunar J. Blumberg; Robert J. Wagner; Frank J. Sroka

[57] ABSTRACT

A process is disclosed for the preparation of aliphatic monocarboxylic acids from primary aliphatic alcohols having 2 to 6 carbon atoms wherein the reaction is in semi-continuous or continuous mode. Acetic acid is prepared from ethanol in high conversion, selectivity and yield. Acetic acid is useful as a solvent for the manufacture of terephthalic acid and other organic compounds.

13 Claims, No Drawings

LIQUID PHASE OXIDATION OF ALCOHOLS TO PREPARE CARBOXYLIC ACIDS

This is a continuation-in-part of application Ser. No. 672,970, filed Mar. 21, 1991, now abandoned, which is a continuation-in-part of application Ser. No. 279,429 filed Dec. 2, 1988, now abandoned.

FIELD OF THE INVENTION

This invention relates to an improved process for preparing carboxylic acids from their corresponding primary alkanols, e.g., ethyl alcohol to acetic acid. More specifically, it relates to an improved process for the semicontinuous or continuous preparation of a primary aliphatic carboxylic acid from its corresponding alkanol in a liquid phase process in the presence of a cobalt-manganese-bromine catalyst to yield the aliphatic carboxylic acid in high conversion, selectivity and yield. Carboxylic acids, particularly acetic acid, have many uses. For example, acetic acid is used as a solvent in manufacture of terephthalic acid in the preparation of polyester compounds, and as a solvent or reagent in the preparation of plastics, elastomers, pharmaceuticals, dyes, insecticides and other organic and inorganic chemicals.

BACKGROUND OF THE INVENTION

Acetic acid, one of the more important aliphatic intermediates, quantitatively ranks among the commodity chemicals produced in large tonnage quantities. However, availability of acetic acid for downstream applications can be limited at times since availability and price of feedstocks for the production of acetic acid are subject to constant change. For example, availability of hydrocarbon feedstocks such as ethylene, butane and butenes from petroleum sources and natural gas can vary widely depending upon supplies of crude oil upon the world market, capacity of petrochemical producers and demand for products which utilize these same hydrocarbons as feedstocks. An example is polyethylene from ethylene.

Acetic acid can be manufactured by one of several processes, i.e., from acetaldehyde or alkanes and alkenes by oxidation, by carbonylation of methanol, among others. Some of these other processes include the oxidizing of methylcyclohexane to produce acetic acid and formic acid, U.S. Pat. No. 3,247,249; oxidation of ethyl alcohol in the presence of a solid palladium metal containing catalyst, U.S. Pat. No. 3,739,020; oxidation of ethyl alcohol in the presence of at least one ketone such as methylethyl ketone and at least one aldehyde such as acetaldehyde and using air, cobalt acetate catalyst and acetic acid reaction medium, U.S. Pat. No. 3,914,296.

It is well-known that carboxylic acids such as acetic acid can be produced by several liquid phase processes including the liquid phase oxidation of various organic compounds, such as ethanol to acetic acid. For example, in U.S. Pat. No. 2,425,878, a liquid phase oxidation process involves the direct reaction of a lower aliphatic alcohol, ethanol, with oxygen in a liquid phase reaction to prepare acetic acid wherein a rare earth metal catalyst is activated by an aldehyde. Large amounts of catalyst and activator are required.

In the past, high rates of conversion have been obtained in the utilization of ethanol to prepare acetic acid by use of an activator or promoter, as for example, when an aldehyde such as acetaldehyde is used as an activator, as in U.S. Pat. No. 2,578,306.

Although excellent yields of acetic acid are obtained, large amounts of promoter are required, from 1.6 to 9 moles acetaldehyde/mole ethanol oxidized (see U.S. Pat. No. 2,578,306), and from 0.41 to 1.26 moles, acetaldehyde plus methylethyl ketone/mole ethanol, oxidized (see U.S. Pat. No. 3,914,296). The problem with using such large amounts of acetaldehyde and methylethyl ketone to prepare acetic acid from ethanol is, while these compounds oxidize to form acetic acid themselves, these compounds cost more than ethanol or acetic acid and are not commercially available in large enough amounts to make a large scale ethanol to acetic acid process practical. The instant invented process uses a cobalt, manganese, and bromine catalyst system and does not require additional promoters.

Oxidation of ethanol to acetic acid using a cobalt, manganese, bromide catalyst is taught in U.S. Pat. No. 3,247,249, "Preparation of Formic and Acetic Acids by Oxidizing Methylcyclohexane or Paraffin Wax in the Presence of Manganese Bromide." The yield of acetic acid and selectivity to acetic acid are far lower using the reaction conditions described in U.S. Pat. No. 3,247,249 than yields obtained by other processes, including yields obtained by processes using an activator or promoter. Yields of acetic acid given in the examples range from 12 to 19 mole % with formic acid being the major product in 61 to 64 mole % yield.

It has been discovered that utilization of a cobalt-manganese-bromine-containing catalyst without added promoters in a semi-continuous or continuous method makes possible the production of aliphatic carboxylic acids in high conversion, good selectivity and yield from primary aliphatic alcohols. By utilizing different primary aliphatic alcohols as feed, it is possible to obtain the corresponding carboxylic acid, as for example, acetic acid from ethanol, propionic acid from n-propanol, n-butyric acid from n-butanol, etc.

In contrast to the low yields reported in U.S. Pat. No. 3,247,249, under the process conditions of the instant invented process, acetic acid yields of 65 mole % are achieved, and formic acid yield is minimized to as low as 1 mole % with consequent increased yield of acetic acid.

It is therefore an object of the present invention to provide an improved process for the preparation of aliphatic monocarboxylic acids from their corresponding primary alcohol wherein yield of the resulting acid is in good yield in the absence of a promoter or accelerator, although an accelerator can be used.

It is an object of this invention to provide an improved process for the preparation of an aliphatic monocarboxylic acid having from two to six carbon atoms wherein the process is in a liquid phase, semi-continuous or continuous mode, and the catalyst is a cobalt-manganese-bromine catalyst.

It is further an object of this invention to provide an improved process for preparation of acetic acid from ethanol by oxidation in a semi-continuous or continuous mode in the presence of a cobalt-manganese-bromine catalyst wherein reaction progress is controlled as a function of residence time to obtain a good yield of acetic acid and to minimize production of by-products.

SUMMARY OF THE INVENTION

A process is disclosed for preparation of aliphatic monocarboxylic acids from primary aliphatic alcohols having from two to six carbon atoms in a semicontinuous or continuous mode. Acetic acid is prepared from ethanol in high selectivity, conversion and yield.

DETAILS OF THE INVENTION

While the most preferred embodiment of the present invention is illustrated in the production of acetic acid from ethanol, other carboxylic acids can be produced similarly from corresponding alcohols.

The carboxylic acids which can be produced in accordance with the present invention include lower aliphatic monocarboxylic acids of the formula RCOOH wherein R is an alkyl group of 1 to 6 carbon atoms. Non-limiting examples of such carboxylic acids include acetic acid, propionic acid, butyric acid, valeric acid, hexanoic acid and the like. Acetic acid and propionic acid are particularly suitable.

Alcohols which can be subjected to liquid phase oxidation processes to produce carboxylic acids are well-known. Such alcohols include lower aliphatic alcohols represented by the formula R—OH wherein R is an alkyl group of 2 to 6 carbon atoms, preferably 2 to 5 carbon atoms. Ethanol is particularly preferred. Other non-limiting examples of such alcohols include n-propyl alcohol, n-butyl alcohol, amyl alcohol, n-hexyl alcohol, and the like.

Preferably, in accordance with the process of this invention, a continuously fed stirred-tank reactor (CSTR) is fed under isothermal conditions wherein reaction progress is controlled as a function of reactor residence time. Residence time is defined as reactor volume divided by volumetric effluent rate. Preferably the process of this invention is operated as a continuous-flow operation although a semi-continuous or semi-batch operation wherein the reactant is added during the course of the reaction can be utilized. A batch operation wherein reactant and catalyst are reacted as a single charge to the reactor is unsuitable for the process of this invention.

It is preferable for the process of this invention that a continuous-flow stirred reactor be utilized to obtain maximum yield of the desired carboxylic acid, although the process can be operated in a semi-continuous method. It is preferred that the continuous-flow stirred reactor be operated in a steady state, that is, the composition of the effluent remains constant with time and that flow rate, reaction temperature and feed composition remain constant so that residence time of reactant in the reaction remains constant.

Progress of the reaction wherein ethanol is oxidized can comprise a series of reactions wherein the sequence is:

  1)

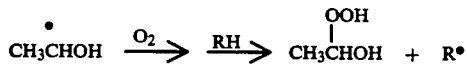  2)

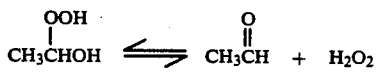  3)

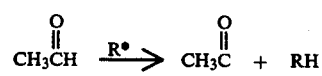  4)

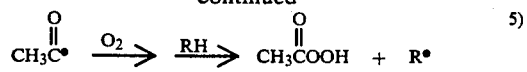  5)

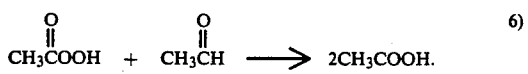  6)

Essential elements of the process of the instant invention accordingly include volumetric rate of effluent relative to reactor volume and hence residence time, catalyst concentration, reaction temperature and reaction pressure, and the interrelationships which exist among these elements in a semi-continuous or continuous method.

A wide variety of compounds can be utilized as solvent for the reaction. Desirably there can be utilized in the reaction mixture, as a solvent or diluent, a monocarboxylic acid having from 2 to 6 carbon atoms of the same composition as the desired product.

Suitable solvents for use in the method of this invention include any aliphatic $C_2$–$C_6$ monocarboxylic acid such as acetic acid, propionic acid, n-butyric acid, isobutyric acid, n-valeric acid, trimethylacetic acid and caproic acid, and mixtures of the solvents with water. Preferably, the solvent is a mixture of acetic acid and water, which more preferably contains from about 1 to about 30 weight percent of water, as introduced into the oxidation reactor. Since heat generated in the highly exothermic liquid phase oxidation is dissipated at least partially by vaporization of solvent in the oxidation reactor, some of the solvent is withdrawn from the reactor as a vapor, which is then condensed and partially recycled to the reactor. The remainder is dehydrated to produce acetic acid suitable for aromatic feedstock oxidation. In addition, a product stream is taken from the reactor. The stream is treated to recover the product, recycle the catalyst, and to purge by-products and impurities. The feed weight ratio of the total amount of solvent to the amount of the lower aliphatic alcohol introduced into the reactor in the liquid phase oxidation of this invention is in the range of from about 10:1 to about 0.1:1, preferably from about 3:1, to about 5:1.

The source of molecular oxygen employed in the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing less than 8 volume percent oxygen (measured on a solvent-free basis). For example, when the alcohol is ethyl alcohol a feed rate of the amount of from 1.0 to 1.4 moles oxygen per mole of alcohol will provide such 0.5 to 8 volume percent of oxygen (measured on a solvent-free basis) in the gas-vapor mixture in the condenser.

The catalyst employed in the method of this invention comprises cobalt, manganese and bromine components, and can additionally comprise accelerators known in the art. The weight ratio of cobalt (calculated as elemental cobalt) in the cobalt component of the catalyst to alcohol ratio in the liquid phase oxidation of the method of this invention is in the range of from about 0.2 to about 100 milligram atoms (mga) per gram mole of alcohol. The weight ratio of manganese (calculated as elemental manganese) in the manganese component of the catalyst-to-cobalt (calculated as elemental cobalt) in the cobalt component of the catalyst in the liquid phase oxidation of the method of this invention is in the range of from about 0.2 to about 10 mga per mga of cobalt. The weight ratio of bromine (calculated as elemental bromine) in the bromine component of the catalyst to total cobalt and manganese (calculated as elemental cobalt and elemental manganese) in the cobalt and manganese components of the catalyst in the liquid phase oxidation of the method of this invention is in the range of from about 0.2 to about 1.5 mga per mga of total cobalt and manganese. Each of the cobalt and manganese components can be provided in any of its known ionic or combined forms that provide soluble forms of cobalt, manganese and bromine in the solvent in the reactor. For example, when the solvent is an acetic acid medium, cobalt and/or manganese carbonate, acetate tetrahydrate, and/or bromide can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzyl-bromide, mono-and di-bromoacetic acid, bromoacetyl bromide, tetrabromoethane, ethylene-di-bromide, etc.). The total bromine in molecular bromine and ionic bromide is used to determine satisfaction of the elemental bromine to total cobalt and manganese milligram atom ratio of 0.2:1.0 to 1.5:1.0. The bromide ion released from the organic bromides at the oxidation operation conditions can be readily determined by known analytical means. Tetrabromoethane, for example, at operating temperatures such as 170° to 225° C. has been found to yield about 3 effective gram atoms of bromine per gram mole.

In operation, the minimum pressure at which the reactor is maintained is that pressure which will maintain a substantial liquid phase at the desired oxidation temperature. The alcohol and solvent not in the liquid phase because of vaporization is removed from the reactor as a vapor-gas mixture, condensed and then returned to the reactor. When the solvent is an acetic acid-water mixture, suitable reaction gauge pressures are in the range of from about 0 kg/cm$^2$ to about 35 kg/cm$^2$, and typically are in the range of from about 10 kg/cm$^2$ to about 30 kg/cm$^2$. The temperature range within the reactor is generally from about 194° F. (90° C.), more preferably from about 300° F. (150° C.), to about 460° F. (240° C.), more preferably from about 380° F. (192° C.) to about 400° F. (204° C.).

The oxidation temperature can range from about 194° F. (90° C.) to about 460° F. (240° C.). Air, oxygen, or oxygen-containing gas can be used. Reaction pressures ranging from atmospheric pressure to 450 psig and acetic acid or other carboxylic acids as solvents can be used. Reaction conditions preferred, but not limited to these reaction conditions, are 380° F.–400° F., 190–350 psig pressure, air as the oxygen source, and acetic acid solvent. Concentrations of the cobalt, manganese, bromine catalyst can range from about 0.0002 g (Co+Mn)/g ethanol to about 0.1 g (Co+Mn)/g ethanol with preferred (Co+Mn) concentration of about 0.0036 g/g ethanol to about 0.0143 g/g ethanol. Preferred bromine to (Co+Mn) molar ratio is about 0.5 to about 1.0 Br/(Co+Mn). The reaction can be run in the semi-continuous or continuous mode.

Ethanol residence time in the continuous oxidations can be in the range of about 20 minutes to about four hours, preferably from about 30 to about 90 minutes. Much shorter residence times require severe reaction conditions to obtain high ethanol conversion and are expected to increase feedstock burning and by-product losses. Much longer residence times require larger vessel sizes and therefore increase capital costs.

In summary, suitable operating conditions and preferred operating conditions for continuous and semi-continuous oxidations of ethanol to acetic acid cover a wide range. Suitable solvents are $C_2$ to $C_6$ monocarboxylic acids, and mixtures of these solvents with water, with the preferred solvent being acetic acid containing about 1 to about 30 wt % water. Suitable feed weight ratios of solvent to alcohol are from about 10:1 to about 0.1:1 and the preferred range is about 3:1 to about 5:1. The preferred source of oxygen is air, and a range of about 0.5 and about 8 volume percent in the vent is preferred based on vapor flammability considerations. Total cobalt and manganese catalyst concentrations of about 0.2 to about 100 milligram per gram of alcohol are suitable with about 4 to about 14 milligram metals per gram ethanol preferred. Suitable ranges of manganese to cobalt weight ratio are from about 0.2:1 to about 10:1. A suitable range of bromine to total cobalt and manganese atom ratio is from about 0.2:1 to about 1.5:1. Suitable oxidation temperatures are from about 194° F. to about 460° F. with about 380° F. to about 400° F. being preferred. The ethanol residence time in the continuous oxidations should be in the range of about 20 minutes to about four hours, preferably from about 30 to about 90 minutes.

In summary, the instant invented process comprises a semi-continuous or continuous process for preparation of aliphatic monocarboxylic acids having from 2 to 6 carbon atoms from aliphatic primary alcohol wherein the process comprises: a) injecting into a suitable reactor a solvent comprising an aliphatic monocarboxylic acid having from 2 to 6 carbon atoms or a mixture of the monocarboxylic acid and water and a primary aliphatic alcohol having from 2 to 6 carbon atoms, b) oxidizing the primary aliphatic alcohol having from 2 to 6 carbon atoms with an oxygen-containing gas in the presence of a cobalt-manganese bromine catalyst wherein total concentration of cobalt and manganese catalyst metals to concentration of the primary aliphatic alcohol is in the range of from about 0.2 to about 100 milligrams per gram of the primary aliphatic alcohol having a temperature within the range of from about 194° F. to about 460° F., reaction pressure is from atmospheric to about 450 psig, and residence time of the primary aliphatic alcohol is from about 20 minutes to about 4 hours, and c) separating an aliphatic monocarboxylic acid having from 2 to 6 carbon atoms from oxidation products of the process.

The invention further comprises a process where in weight ratio of cobalt, calculated as elemental cobalt, in the cobalt component of the catalyst is in the range of from about 0.2 to about 100 milligram atoms per gram mole of the alcohol, weight ratio of manganese, calculated as elemental manganese in the catalyst component of the catalyst to cobalt, calculated as elemental cobalt, is in the range of from about 0.2 to about 10 milligram atoms per milligram atom of cobalt and weight ratio of bromine as the bromine component of the catalyst to total cobalt and manganese, calculated as elemental cobalt and manganese, in the cobalt and manganese components of the catalyst is in the range of from about 0.2 to about 1.5 milligram atoms per milligram atoms of total cobalt and manganese. In more detail, the solvent can comprise a mixture of water and the primary alcohol having from 2 to 6 carbon atoms and the solvent contains from about 1 to about 30 wt % water. The weight ratio of the solvent to the primary aliphatic alcohol having from 2 to 6 carbon atoms can be from about 10:1 to about 0.1:1. Preferably the process of the weight ratio of the solvent to the primary aliphatic alcohol is from about 3:1 to about 5:1. Preferably, the oxygen-containing gas is air. The process wherein the catalyst concentration is from about 4 to about 14 milligrams of catalyst metals per gram of primary aliphatic alcohol having 2 to 6 carbon atoms, the process ratio of bromine to total cobalt and manganese is from about 0.2:1 to about 1.5:1. Preferably, the temperature is in the range of from about 380° F. to about 400° F., the residence time is in the range of from about 30 to about 90 minutes, and the primary aliphatic alcohol is ethanol.

A semi-continuous or continuos process for preparation of aliphatic monocarboxylic acids having from 2 to 6 carbon atoms from aliphatic primary alcohols having from 2 to 6 carbon atoms which process comprises:

a) injecting into a suitable reactor a primary aliphatic alcohol having from 2 to 6 carbon atoms and a solvent selected from the group consisting of an aliphatic monocarboxylic acid having from 2 to 6 carbon atoms and a mixture of the aliphatic monocarboxylic acid having from 2 to 6 carbon atoms and water of from about 1 weight percent water up to about 30 weight percent water.

b) oxidizing in the presence of the solvent selected from the group consisting of an aliphatic monocarboxylic acid having from 2 to 6 carbon atoms and a mixture of the aliphatic monocarboxylic acid having from 2 to 6 carbon atoms and water from about 1 weight percent water up to about 30 weight percent water the primary aliphatic alcohol having from 2 to 6 carbon atoms with a source of molecular oxygen as a gas in a liquid phase oxidation in the presence of a catalyst comprising cobalt, manganese and bromine components wherein each of the cobalt, manganese and bromine catalyst components provide soluble forms of cobalt, manganese and bromine in the solvent, the weight ratio of cobalt, calculated as elemental cobalt, in the cobalt component to ratio of the alcohol is in the range of from about 0.2 to about 100 milligram atoms per gram mole of the alcohol, the weight ratio of manganese, calculated as elemental manganese, in the manganese component to cobalt component in the catalyst is in the range of from about 0.2 to about 10 milligram atoms per milligram atoms of cobalt, the weight ratio of bromine, calculated as elemental bromine, in the bromine component to total cobalt and manganese in the cobalt and manganese components of the catalyst is in the range of from about 0.2:1.0 to about 1.5:1.0 milligram atoms per milligram atoms of total cobalt and manganese, reaction pressure is in the range from atmospheric to about 450 psig, temperature is in the range of from about 194° F. (90° C.) to about 460° F. (240° C.), and the feed weight ratio, as introduced into the reactor, of total amount of the solvent to the amount of the primary aliphatic alcohol is in the range of from about 10:1 to about 0.1:1.

The instant invention will be more clearly understood from the following examples which are merely illustrative and not limitative of the scope of the invention.

EXAMPLE I

This example was done to simulate a CSTR with a 68-minute residence time since for higher conversions of ethanol such a procedure is considered a valid simulation.

Acetic acid was prepared by semi-continuous oxidation of ethanol in a one-liter titanium clad autoclave. The oxidation catalyst, consisting of 1.65 g Co(OAc)$_2$ tetrahydrate, 4.20 g Mn(OAc)$_2$ tetrahydrate and 1.98 g 48 wt. percent HBr was dissolved in a solvent mixture consisting of 388 g acetic acid and 10 g water. The reactor charge was heated to 400° F. and pressurized to 350 psi. When the temperature and pressure were attained, addition of ethanol and air began. One hundred and seventy ml of 93 wt. % aqueous ethanol were added over 68 minutes. When addition of ethanol was complete the reaction was quenched. The yield of free acetic acid, after subtracting out the acetic acid initially added in the reactor charge, was 65 mole % based on the ethanol added. Additional acetic acid (6 mole %) was present as acetate esters. By recycling unreacted ethanol, acetaldehyde, and the ethanol and acetic acid present as by-product esters, a yield of 76 mole % can result. The data on yield, intermediates and by-products is listed in Table 1.

EXAMPLE II

The reaction procedure was the same as in Example I, except that the reaction temperature was 382° F., the reaction pressure was 250 psi, and the catalyst loading was increased to 2.20 g Co(OAc)$_2$ tetrahydrate, 5.60 g Mn(OAc)$_2$ tetrahydrate, and 2.64 g 48 wt percent HBr. The yield of free acetic acid, after subtracting out the acetic acid initially added in the reactor charge, was 59 mole % based on the ethanol added. Additional acetic acid (10 mole %) was present as acetate esters. By recycling unreacted ethanol, acetaldehyde, and the ethanol and acetic acid present as by-product esters, a yield of 79 mole % can result. The data on yield, intermediates and by-products is listed in Table 1.

EXAMPLE III

The reaction procedure was the same as in Example I, except that the reaction temperature was 382° F. and the pressure was 250 psi. The yield of free acetic acid, after subtracting out the acetic acid initially added in the reactor charge, was 56 mole % based on the ethanol added. Additional acetic acid (10 mole %) was present as acetate esters. The yield with recycle of ethanol, acetaldehyde, and the ethanol and acetic acid present as by-product esters, can be as high as 77 mole %. The data on yield, intermediates and by-products is listed in Table 1.

EXAMPLE IV

The reaction procedure was the same as in Example III, except that the catalyst loading was decreased to 1.10 g Co(OAc)$_2$ tetrahydrate, 2.80 g Mn(OAc)$_2$ tetrahydrate, and 1.32 g 48 wt percent HBr. The yield of free acetic acid, after subtracting out the acetic acid initially added in the reactor charge, was 53 mole % based on the ethanol added. Additional acetic acid (10 mole %) was present as acetate esters. The yield with recycle of ethanol, acetaldehyde, and the ethanol and acetic acid present as by-product esters, can be as high as 74 mole %. The data on yield, intermediates and by-products is listed in Table 1.

EXAMPLE V

The reaction procedure was the same as in Example IV, except that catalyst loading was decreased to 0.55 g Co(OAc)$_2$ tetrahydrate, 1.40 g Mn(OAc)$_2$ tetrahydrate, and 0.66 g 48 wt percent HBr, and the reaction pressure was 205 psi. The yield of free acetic acid, after subtracting out the acetic acid initially added in the reactor charge, was 43 mole % based on the ethanol added. Additional acetic acid (17 mole %) was present as acetate esters. The yield with recycle of ethanol, acetaldehyde, and the ethanol and acetic acid present as by-product esters, can be as high as 82 mole %. The data on yield, intermediates and by-products is listed in Table 1.

EXAMPLE VI

The reaction procedure was the same as in Example V, except that no water was added initially with the reactor charge. The yield of free acetic acid, after subtracting out the acetic acid initially added in the reactor charge, was 47 mole % based on the ethanol added. Additional acetic acid (12 mole %) was present as acetate esters. The yield with recycle of ethanol, acetaldehyde, and the ethanol and acetic acid present as by-product esters, can be as high as 75 mole %. The data on yield, intermediates and by-products is listed in Table 1.

EXAMPLE VII

The following example emphasizes the unacceptable level of production of formic acid resulting from batch mode of operation versus greatly improved production of acetic acid and low production of formic acid obtained in the semi-continuous mode and presence of a cobalt-manganese-bromine catalyst of Examples I to VI.

Acetic acid was prepared by batch oxidation of ethanol in a one-liter titanium clad autoclave. One hundred and seventy ml of 93 wt. % aqueous ethanol, acetic acid, 388 g, cobalt acetate tetrahydrate, 0.55 g, manganese acetate tetrahydrate, 1.40 g and 48 wt percent HBr, 0.66 g were combined in the autoclave. The mixture was heated to 194° C. and pressurized to 300 psi before adding air. Oxidation proceeded for 130 minutes. Residence time was 130 minutes. Analysis of the reaction product showed that the yield of free acetic acid after subtracting out the acetic acid initially added in the reactor charge, was 2 mole % based on the ethanol added. Additional acetic acid (15 mole %) was present as acetate esters. The yield with recycle of ethanol, acetaldehyde, and the ethanol and acetic acid present as by-product esters, can be as high as 33 mole %. Formic acid was formed as a substantial by-product in 12.5 percent yield, including free formic acid (11.5 mole percent), ethyl formate (1.0 mole percent) and methyl formate (0.017 mole percent). The data on yield, intermediates and by-products are listed in Table 1.

TABLE 1

Reaction Yields and Distribution of By-products from Semi-continuous and Batch Ethanol Oxidations

| | Example | | | | | | |
|---|---|---|---|---|---|---|---|
| | I | II | III | IV | V | VI | VII |
| Process | SC | SC | SC | SC | SC | SC | B |
| Single Pass Yield of Free Acetic Acid, mole % | 65 | 59 | 56 | 53 | 43 | 47 | 2 |
| % of Ethanol Oxidized to Acetic Acid | 71 | 69 | 66 | 63 | 60 | 59 | 17 |
| Yield With Recyle | 76 | 79 | 77 | 74 | 82 | 75 | 33 |
| Yield Losses in Mother Liquor, mole % | | | | | | | |
| Unreacted Ethanol | 0.77 | 1.60 | 1.92 | 0.91 | 5.33 | 3.66 | 2.54 |
| Ethyl Acetate | 9.94 | 17.3 | 17.8 | 18.5 | 31.9 | 23.1 | 26.1 |
| Acetaldehyde | 0.02 | 0.19 | 0.14 | 0.14 | 0.40 | 0.29 | 0.15 |
| Methyl Acetate | .789 | .680 | .607 | .506 | .472 | .471 | .595 |
| Ethyl Formate | .088 | .331 | .421 | .467 | 1.17 | 1.14 | 2.87 |
| Formic Acid | 1.00 | 1.80 | 1.85 | 1.90 | 2.81 | 2.15 | 11.5 |
| Glycolic Acid | .047 | .007 | .013 | .010 | .021 | .021 | .030 |
| Methanol | .065 | .030 | .005 | .010 | .011 | .010 | .004 |
| Methyl Formate | .009 | .017 | .065 | .010 | .018 | .012 | .034 |
| Yield Losses in Vent and Traps, Mole % | | | | | | | |
| CO + CO$_2$ | 6.3 | 5.9 | 5.0 | .39 | .30 | 2.8 | 10 |
| Acetaldehyde | .08 | .087 | .003 | .003 | .007 | .015 | .014 |
| MeOAc/Ethyl Formate | .079 | .075 | .29 | .28 | .40 | .30 | 1.6 |
| Methyl Formate | .004 | .005 | .05 | .05 | .03 | .05 | .06 |
| Ethyl Acetate | .36 | .63 | .21 | .38 | .34 | .17 | .76 |
| Ethanol | .008 | .013 | .018 | .026 | .026 | .007 | .11 |
| Formic Acid | .002 | .002 | .003 | .005 | .001 | .003 | .012 |
| Methane | .010 | .013 | .010 | .023 | .012 | .012 | .32 |
| Acetic Acid | 1.34 | 1.47 | 1.29 | 1.66 | 1.70 | 1.70 | 1.06 |

NOTE:
SC - Semi-Continuous Oxidation
B - Batch Oxidation

EXAMPLE VIII

The following example illustrates that continuous oxidation of ethanol to acetic acid in the process of instant invention resulted in a yield of approximately 60 mole percent of acetic acid. About 3 mole percent of formic acid was produced. Two oxidations, A and B, were made. Acetic acid was prepared by the continuous oxidation of ethanol in a pilot plant equipped with a two-gallon titanium reactor. Reaction conditions used, i.e., catalyst composition and concentration, water concentration, temperature, pressure, residence time and concentration of ethanol in the feed, are summarized in Table 2. Results show that 97 mole percent of the ethanol reacted, 19 mole percent to ethyl acetate (with 18 mole percent staying in the total reactor effluent, TRE), 10 mole percent to carbon oxides, and 5 to 6 mole percent to other burning by-products. As determined by difference, 60 mole percent of the ethanol was converted to acetic acid. Based on the above results, an overall process yield of 83 mole percent is expected, i.e., by recycle of the unreacted ethanol and ethyl acetate in the reactor effluent. By-product component distributions are summarized in Table 3.

TABLE 2

| Reaction Conditions for Continuous Oxidations | | |
|---|---|---|
| Oxidation | A | B |
| Cobalt, ppmw in TRE | 285 | 288 |
| Mn/Co, Moles | 2.55 | 2.54 |
| Br/(Mn + Co), Moles | 0.466 | 0.446 |
| Water, wt. % in TRE | 13.6 | 12.8 |
| Temperature, °F. | 382 | 386 |
| Pressure, psig | 250 | 258 |
| Residence Time, min. | 66 | 65 |
| Feed EtOH Conc., wt. % | 25 | 26 |

Note:
Mn manganese
Co cobalt
Br bromine
EtOH ethanol
TRE total reactor effluent
ppmw parts per million by weight

TABLE 3

| Products of Continuous Ethanol Oxidations in Mole % | | |
|---|---|---|
| Oxidation | A | B |
| Acetic Acid* | 63.3 | 61.9 |
| Ethyl Acetate | 19.4 | 19.4 |
| Carbon Oxides | 9.5 | 10.4 |
| Ethanol in TRE | 3.2 | 3.2 |
| Formic Acid in TRE | 2.8 | 3.1 |
| Methyl acetate/ ethyl formate | 1.8 | 1.8 |
| Acetaldehyde | 0.2 | 0.2 |

*By difference

We claim:

1. A semi-continuous or continuous process for preparation of aliphatic monocarboxylic acids having from 2 to 6 carbon atoms from aliphatic primary alcohols having from 2 to 6 carbon atoms which process comprises:
   a) injecting into a suitable reactor a primary aliphatic alcohol having from 2 to 6 carbon atoms and a solvent selected from the group consisting of an aliphatic monocarboxylic acid having from 2 to 6 carbon atoms and a mixture of the aliphatic monocarboxylic acid having from 2 to 6 carbon atoms and water of from about 1 weight percent water up to about 30 weight percent water,
   b) oxidizing in the presence of the solvent selected from the group consisting of an aliphatic monocarboxylic acid having from 2 to 6 carbon atoms and a mixture of the aliphatic monocarboxylic acid having from 2 to 6 carbon atoms and water from about 1 weight percent water up to about 30 weight percent water the primary aliphatic alcohol having from 2 to 6 carbon atoms with a source of molecular oxygen as a gas in a liquid phase oxidation in the presence of a catalyst comprising cobalt, manganese and bromine components wherein each of the cobalt, manganese and bromine catalyst components provide soluble forms of cobalt, manganese and bromine in the solvent, the weight ratio of cobalt, calculated as elemental cobalt, in the cobalt component to ratio of the alcohol is in the range of from about 0.2 to about 100 milligram atoms per gram mole of the alcohol, the weight ratio of manganese, calculated as elemental manganese, in the manganese component to cobalt component in the catalyst is in the range of from about 0.2 to about 10 milligram atoms per milligram atoms of cobalt, the weight ratio of bromine, calculated as elemental bromine, in the bromine component to total cobalt and manganese in the cobalt and manganese components of the catalyst is in the range of from about 0.2:1.0 to about 1.5:1.0 milligram atoms per milligram atoms of total cobalt and manganese, reaction pressure is in the range from atmospheric to about 450 psig, temperature is in the range of from about 194° F. (90° C.) to about 460° F. (240° C.), and the feed weight ratio, as introduced into the reactor, of total amount of the solvent to the amount of the primary aliphatic alcohol is in the range of from about 10:1 to about 0.1:1.

2. The process of claim 1 wherein the primary aliphatic alcohol is selected from the group consisting of ethyl alcohol, n-propyl alcohol, n-butyl alcohol, amyl alcohol, and n-hexyl alcohol.

3. The process of claim 1 wherein the primary aliphatic alcohol is ethyl alcohol.

4. The process of claim 1 wherein the aliphatic monocarboxylic acid is selected from the group consisting of acetic acid, propionic acid, n-butyric acid, isobutyric acid, n-valeric acid, trimethylacetic acid and caproic acid.

5. The process of claim 1 wherein the aliphatic monocarboxylic acid is acetic acid.

6. The process of claim 1 wherein the feed weight ratio of total amount of the solvent to the amount of the primary aliphatic alcohol is in the range of from about 3:1 to about 5:1.

7. The process of claim 1 wherein the source of the molecular oxygen is in an oxygen-containing gas comprising air.

8. The process of claim 1 wherein the solvent comprises acetic acid and the soluble forms of cobalt, manganese and bromine components of the catalyst are selected from cobalt carbonate, cobalt acetate tetrahydrate, cobalt bromide, manganese carbonate, manganese acetate tetrahydrate, manganese bromide, elemental bromine, ionic bromides, and organic bromides selected from the group consisting of bromobenzenes, benzylbromide, monobromoacetic acid, dibromoacetic acid, bromoacetyl bromide, tetrabromoethane, and ethylene dibromide.

9. The Process of claim 1 wherein the process is a continuous process, the primary aliphatic alcohol is ethyl alcohol and residence time in the continuous oxidation is in the range of from about 20 minutes to about 4 hours.

10. The process of claim 9 wherein the residence time is in the range of from about 30 minutes to about 90 minutes.

11. The process of claim 1 wherein the temperature is in the range of from about 380° F. to about 400° F., pressure is from about 190 psig to about 350 psig, air is the source of molecular oxygen, the solvent comprises acetic acid, the aliphatic primary alcohol is ethyl alcohol, concentrations of the cobalt, manganese, bromine catalyst range from about 0.0002 g (Co+Mn)g ethyl alcohol to about 0.1 g (Co+Mn)/g ethyl alcohol.

12. The process of claim 11 wherein the concentrations of cobalt, manganese, bromine catalyst range is from about 0.0036 g (Co+Mn)/g ethyl alcohol to about 0.0143 (Co+Mn)/g ethyl alcohol, and range of bromine to (Co+Mn) molar ratio is from about 0.5 to about 1.0 Br/(Co+Mn).

13. The process of claim 1 wherein the weight ratio of the solvent to the primary aliphatic alcohol introduced into the reactor is from about 3:1 to about 5:1, the source of molecular oxygen is air, the catalyst is present in a concentration from about 4 to about 14 milligrams of catalyst metals per gram of the primary aliphatic alcohol process ratio of bromine to total cobalt and manganese is from about 0.2:1 to about 1.5:1, the temperature is in the range of from about 380° F. to about 400° F., residence time is in the range of from about 30 to about 90 minutes, the solvent comprises acetic acid containing 1 to 30 wt % water and the primary aliphatic alcohol is ethyl alcohol.

* * * * *

UNITED STATES PATENT AND TRADEMARK OFFICE
CERTIFICATE OF CORRECTION

PATENT NO. : 5,166,424
DATED : November 24, 1992
INVENTOR(S) : Kristi A. Fjare, Calvin T. Chew It is certified that error appears in the above-indentified patent and that said Letters Patent is hereby corrected as shown below:

COLUMN 10

Table I    "Yield With Recyle" should read --Yield With Recycle--
33

Signed and Sealed this

Fifteenth Day of February, 1994

BRUCE LEHMAN

Attest:

Attesting Officer        Commissioner of Patents and Trademarks